(12) United States Patent
Xu et al.

(10) Patent No.: US 10,947,185 B2
(45) Date of Patent: Mar. 16, 2021

(54) CRYSTAL FORM OF DEZOCINE AND PREPARATION METHOD THEREFOR

(71) Applicant: Yangtze River Pharmaceutical (Group) Co., Ltd., Jiangsu (CN)

(72) Inventors: Jingren Xu, Jiangsu (CN); Wei Cai, Jiangsu (CN); Haoyu Xu, Jiangsu (CN); Ying Xu, Jiangsu (CN); Zhichao Xiao, Jiangsu (CN); Shiwei Yao, Jiangsu (CN)

(73) Assignee: Yangtze River Pharmaceutical Group Co., Ltd., Jiangsu (CN)

( * ) Notice: Subject to any disclaimer, the term of this patent is extended or adjusted under 35 U.S.C. 154(b) by 0 days.

(21) Appl. No.: 16/611,629

(22) PCT Filed: May 22, 2018

(86) PCT No.: PCT/CN2018/087856
§ 371 (c)(1),
(2) Date: Nov. 7, 2019

(87) PCT Pub. No.: WO2018/214877
PCT Pub. Date: Nov. 29, 2018

(65) Prior Publication Data
US 2020/0115321 A1 Apr. 16, 2020

(30) Foreign Application Priority Data
May 22, 2017 (CN) .......................... 2017 1 0362137

(51) Int. Cl.
*C07C 215/64* (2006.01)
*C07C 213/10* (2006.01)

(52) U.S. Cl.
CPC .......... *C07C 215/64* (2013.01); *C07C 213/10* (2013.01); *C07B 2200/13* (2013.01)

(58) Field of Classification Search
None
See application file for complete search history.

(56) References Cited

U.S. PATENT DOCUMENTS

| 3,931,328 A | 1/1976 | Freed et al. |
| 3,937,736 A | 2/1976 | Freed et al. |
| 4,001,331 A | 1/1977 | Freed et al. |

FOREIGN PATENT DOCUMENTS

| CN | 101671269 A | 3/2010 |
| CN | 101678016 A | 3/2010 |

(Continued)

OTHER PUBLICATIONS

Feb. 25, 2020, (CN), Office Action for Application Serial No. CN 201710362137.5.

(Continued)

*Primary Examiner* — Sudhakar Katakam
*Assistant Examiner* — Jennifer C Sawyer
(74) *Attorney, Agent, or Firm* — Banner & Witcoff, Ltd.

(57) ABSTRACT

Disclosed is a crystal form of dezocine. The X-ray powder diffraction (XRD) pattern thereof is determined using Cu/K-α1 and has diffraction peaks at the 2θ value of 9.1±0.2 and 12.2±0.2, with the height % of these diffraction peaks greater than 20. Also disclosed are a preparation method for the crystal form, a pharmaceutical composition and use thereof. The crystal form of dezocine has good solubility, the preparation method has simple operations, good reproducibility, suitability for industrial production and the like.

16 Claims, 4 Drawing Sheets

(56) References Cited

FOREIGN PATENT DOCUMENTS

| CN | 102036946 | A  | 4/2011  |
|----|-----------|----|---------|
| CN | 102503840 | A  | 6/2012  |
| CN | 107522625 | A  | 12/2017 |
| CN | 107778187 | A  | 3/2018  |
| WO | 2007056142 | A2 | 5/2007  |
| WO | 2007087452 | A2 | 8/2007  |
| WO | 2009007110 | A2 | 1/2009  |
| WO | 2014190271 | A2 | 11/2014 |

OTHER PUBLICATIONS

Jun. 25, 2012, Yuan Zhang, Yuancai Zheng, Tongke Chen, Jiayin Zhu, Huiling Zhao & Guanyang Lin, "Determination of Dezocine in Rabbit Plasma by Liquid Chromatography-Mass Spectrometry and its Application", Latin American Journal of Pharmacy.

Oct. 18, 2018, Search Report of Chinese Application No. 2017103621375.

Aug. 20, 2018, International Search Report of PCT/CN2018/087856.

Aug. 14, 2019, Office Action of CN Application No. 201710362137.5.

Apr. 29, 2019, Office Actiion of CN Application No. 201710362137.5.

Oct. 18, 2018, Office Action of CN Application No. 201710362137.5.

CRYSTAL FORM OF DEZOCINE AND PREPARATION METHOD THEREFOR

CROSS-REFERENCE TO RELATED APPLICATIONS

The present application is a U.S. National Phase Entry of International PCT Application No. PCT/CN2018/087856 having an international filing date of May 22, 2018, which claims priority to Chinese Patent Application No. 201710362137.5 filed on May 22, 2017. The present application claims priority and the benefit of the above-identified applications and the above-identified applications are incorporated by reference herein in their entirety.

TECHNICAL FIELD

The present application relates to, but is not limited to, the field of medications, in particular to a new crystal form of dezocine and a preparation method therefor.

BACKGROUND

Dezocine, CAS No.: 32619-42-4, has a chemical name of (−)-[5R-(5α,11α,13S*)]-13-amino-5,6,7,8,9,10,11,12-octahydro-5-methyl-5,11-methanobenzocy clodecen-3-ol, and has the following chemical structural formula:

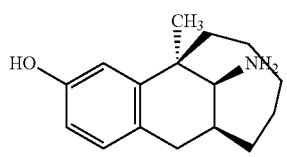

Formula I

Dezocine is developed by Astrazeneca company of Swiss (U.S. Pat. No. 4,001,331) and belongs to a type of typical opioid alkaloid analgesics which not only acts as a κ receptor agonist but also a μ receptor antagonist. Such medication functions as both agonist and antagonist, and exhibits different characteristics by a different receptor subtype affinity than other opioids.

U.S. Pat. 4,001,331 discloses a method for preparing dezocine, various analogues and salt forms thereof; compared with U.S. Pat. No. 4,001,331, Chinese Patent No. CN102503840A is a patent for preparing compounds, in which an oxidant used for preparing intermediate II has better environmental friendliness and economy, and the preparation process for intermediate III has higher safety, higher resolution efficiency, and a simple and efficient process. Chinese Patent No. CN101671269B discloses a method for preparing key intermediates of dezocine, which is simpler to operate, milder in reaction conditions, higher in safety and lower in cost. Chinese Patent No. CN104910002A discloses a method for preparing intermediate V of dezocine, compared with the Patent No. CN102503840A, the synthesis method is simpler and more convenient, the conditions are milder, 7-methoxy-2-tetralone is used as raw material, and the cost is lower; Patent No. DE2159324 discloses a method for preparing dezocine injection; Chinese Patent No. 201510080325.X, which is under the substantive examination, reports an oral formulation of dezocine and a preparation method therefor; Chinese Patent No. 201410405193.9, which is under the substantive examination, discloses a freeze-dried powder injection of dezocine and a preparation method therefor, compared with the injection, the freeze-dried powder injection of dezocine has lower potential safety hazard and better stability; Chinese Patent No. 201410470463.4, which is currently under the substantive examination, discloses a frozen pharmaceutical composition of dezocine and a preparation method therefor, compared with Chinese Patent No. 201410405193.9, the frozen pharmaceutical composition of dezocine has lower impurity content, no organic solvent, safer clinical applications; and Chinese Patent No. 201410804930.2, which is currently under the substantive examination, discloses a method for preparing dezocine injection.

SUMMARY

The following is a summary of the subject matter described in detail herein. This summary is not intended to limit the scope of protection of the claims.

Dezocine has a stronger analgesic effect than pentazocine, less addiction, better safety and tolerance, and is suitable for treating moderate to severe pain after surgery, visceral colic pain and pain of patients with advanced cancer. Its analgesic intensity, onset time, duration of action and maximum analgesic effect are comparable to those of morphine, 5-9 times stronger than those of Dolantin, with slight side effects. At present, raw materials and formulations of dezocine have been marketed for sale in China, as the increasing recognition degree of dezocine in the market and medical institutions, the clinical demand is also continuously increasing.

The patents mentioned in the "Background" section only relate to the synthesis process, intermediate preparation, formulations and other aspects of dezocine and analogues thereof, and do not relate to a crystal form of the compound. Polymorphism is widespread in medications. Different crystal forms of the same medication have significant differences in solubility, melting point, density, stability and other aspects, thus affecting the stability, uniformity, bioavailability, therapeutic effect and safety of the medication to different degrees. Especially in terms of solubility, the existing dezocine medications have extremely poor solubility, which is not conducive to the development of formulations and the absorption of medications in the human body. Therefore, comprehensive and systematic screening of dezocine for crystal forms and selecting crystal forms with high solubility and good stability is one of the important research contents that cannot be ignored. Therefore, the development of a new crystal form of dezocine with better solubility is of great significance for the development of related formulations and the improvement of the bioavailability of dezocine.

The inventors have developed a new crystal form of dezocine, which has fast dissolution, fast absorption by human body, better stability and lower content of related substances during storage; in particular, it does not contain impurity B (chemical structural formula II); moreover, the preparation method for the new crystal form has the advantages such as simple operations, good reproducibility, suitability for industrial mass production and the like.

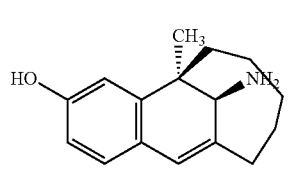

Formula II

In one embodiment of the present application, there is provided a new crystal form of dezocine.

In another embodiment of the present application, there is provided a preparation method for the new crystal form.

In another embodiment of the present application, there is provided a pharmaceutical composition including the new crystal form of dezocine described above.

In another embodiment of the present application, there is provided use of the new crystal form of dezocine or a pharmaceutical composition thereof described above in analgesics.

DETAILED DESCRIPTION

Figure 1A:
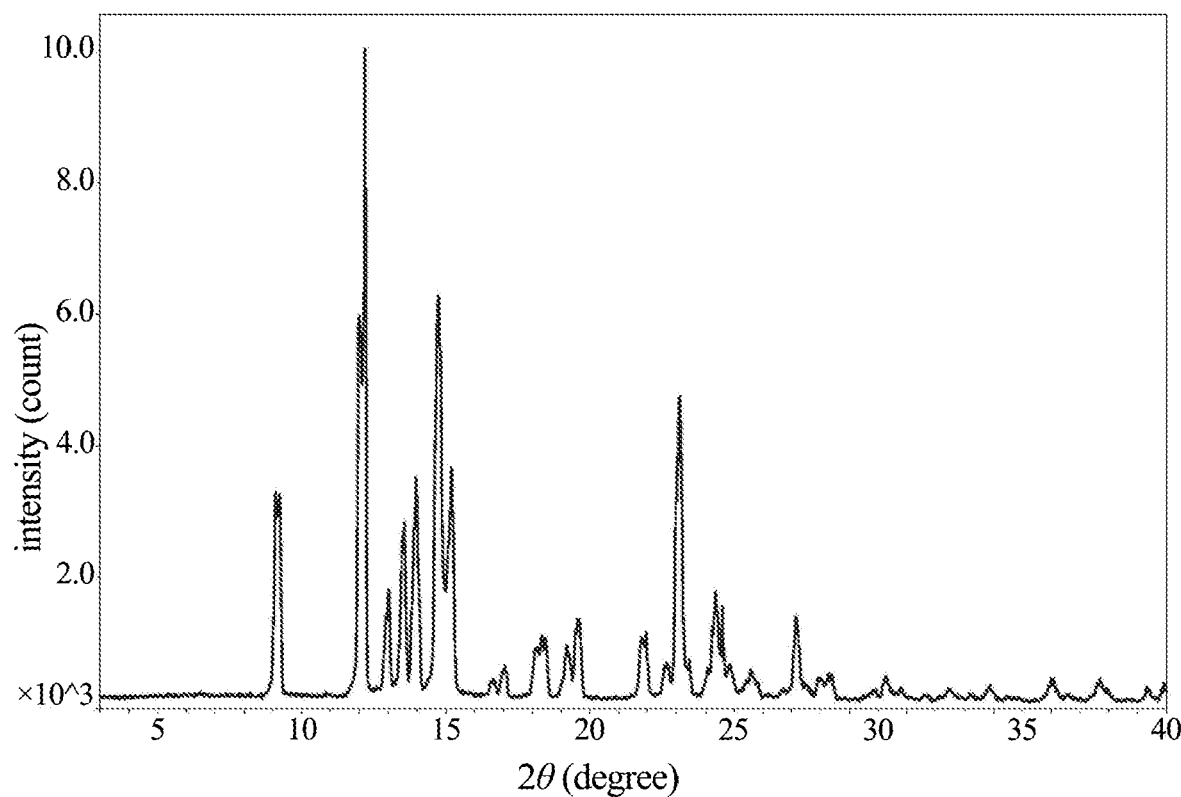
FIG. 1a shows the XRD pattern of the new crystal form of dezocine according to Example 1 of the present application.

In one embodiment of the present application, there is provided a new crystal form of dezocine, the X-ray powder diffraction pattern of the new crystal form is determined using Cu/K-α1 and has diffraction peaks at 2θ value of 9.1±0.2 and 12.2±0.2, with the height % of these diffraction peaks greater than 20.

In one embodiment of the present application, there is provided a new crystal form of dezocine, the X-ray powder diffraction pattern of the new crystal form of dezocine is determined using Cu/K-α1, and may have diffraction peaks at 2θ value of 9.1±0.2, 12.2±0.2, 13.6±0.2, and 23.1±0.2, with the height % of these diffraction peaks greater than 20. In one embodiment of the present application, there is provided a new crystal form of dezocine, the X-ray powder diffraction pattern of the new crystal form of dezocine is determined using Cu/K-α1, and may have diffraction peaks at 2θ value of 9.1±0.2, 12.2±0.2, 13.0±0.2, 13.6±0.2, 14.0±0.2, 14.7±0.2, 15.2±0.2, 19.6±0.2, 23.1±0.2, 24.4±0.2, and 27.2±0.2, with the height % of these diffraction peaks greater than 20.

In one embodiment of the present application, there is provided a new crystal form of dezocine, the X-ray powder diffraction pattern of the new crystal form of dezocine is determined using Cu/K-α1, and may have the following diffraction peak profile:

| Peak number | 2θ | d value | Height % | Area % | FWHM |
| --- | --- | --- | --- | --- | --- |
| 1 | 9.100 | 9.7102 | 51.4 | 66.1 | 0.460 |
| 2 | 12.161 | 7.2716 | 100.00 | 100.0 | 0.358 |
| 3 | 13.008 | 6.8003 | 23.0 | 9.2 | 0.143 |
| 4 | 13.556 | 6.5265 | 41.8 | 22.3 | 0.191 |
| 5 | 13.973 | 6.3329 | 52.2 | 26.2 | 0.179 |
| 6 | 14.743 | 6.0038 | 98.7 | 72.5 | 0.263 |
| 7 | 15.197 | 5.8252 | 56.3 | 44.9 | 0.285 |
| 8 | 16.656 | 5.3183 | 4.2 | 2.5 | 0.208 |
| 9 | 17.051 | 5.1958 | 7.7 | 3.9 | 0.183 |
| 10 | 18.118 | 4.8923 | 12.1 | 9.2 | 0.271 |
| 11 | 18.452 | 4.8043 | 14.7 | 17.4 | 0.424 |
| 12 | 19.186 | 4.6222 | 13.0 | 9.7 | 0.266 |
| 13 | 19.598 | 4.5259 | 19.8 | 12.8 | 0.231 |
| 14 | 21.808 | 4.0720 | 14.8 | 8.4 | 0.202 |
| 15 | 22.675 | 3.9182 | 8.1 | 6.2 | 0.273 |
| 16 | 23.111 | 3.8452 | 74.9 | 42.2 | 0.201 |
| 17 | 23.444 | 3.7914 | 8.9 | 7.9 | 0.318 |
| 18 | 24.355 | 3.6516 | 25.5 | 22.9 | 0.321 |
| 19 | 24.865 | 3.5779 | 6.9 | 5.9 | 0.307 |
| 20 | 25.580 | 3.4794 | 6.0 | 4.7 | 0.276 |
| 21 | 27.159 | 3.2807 | 19.9 | 12.4 | 0.223 |
| 22 | 27.549 | 3.2351 | 3.0 | 3.6 | 0.425 |
| 23 | 28.043 | 3.1792 | 4.5 | 4.2 | 0.337 |
| 24 | 28.281 | 3.1530 | 5.6 | 3.7 | 0.236 |
| 25 | 29.859 | 2.9899 | 1.8 | 1.1 | 0.215 |
| 26 | 30.274 | 2.9498 | 5.9 | 5.1 | 0.311 |
| 27 | 30.773 | 2.9031 | 2.6 | 2.1 | 0.281 |
| 28 | 31.635 | 2.8259 | 1.2 | 0.6 | 0.178 |
| 29 | 32.467 | 2.7554 | 2.7 | 2.1 | 0.275 |
| 30 | 33.201 | 2.6962 | 1.6 | 0.5 | 0.108 |
| 31 | 33.865 | 2.6448 | 3.7 | 2.2 | 0.215 |
| 32 | 34.519 | 2.5962 | 1.1 | 0.8 | 0.271 |
| 33 | 36.000 | 2.4927 | 5.6 | 4.5 | 0.286 |
| 34 | 37.715 | 2.3832 | 5.4 | 4.6 | 0.310 |
| 35 | 39.298 | 2.2908 | 3.3 | 1.5 | 0.158 |

In one embodiment of the present application, there is provided a new crystal form of dezocine, the X-ray powder diffraction pattern of the new crystal form of dezocine is determined using Cu/K-α1, which can be substantially as shown in FIG. 1a.

In one embodiment of the present application, there is provided a new crystal form of dezocine, and a DSC test of the new crystal form of dezocine can show an endothermic peak near 168.40° C.

Figure 2A:
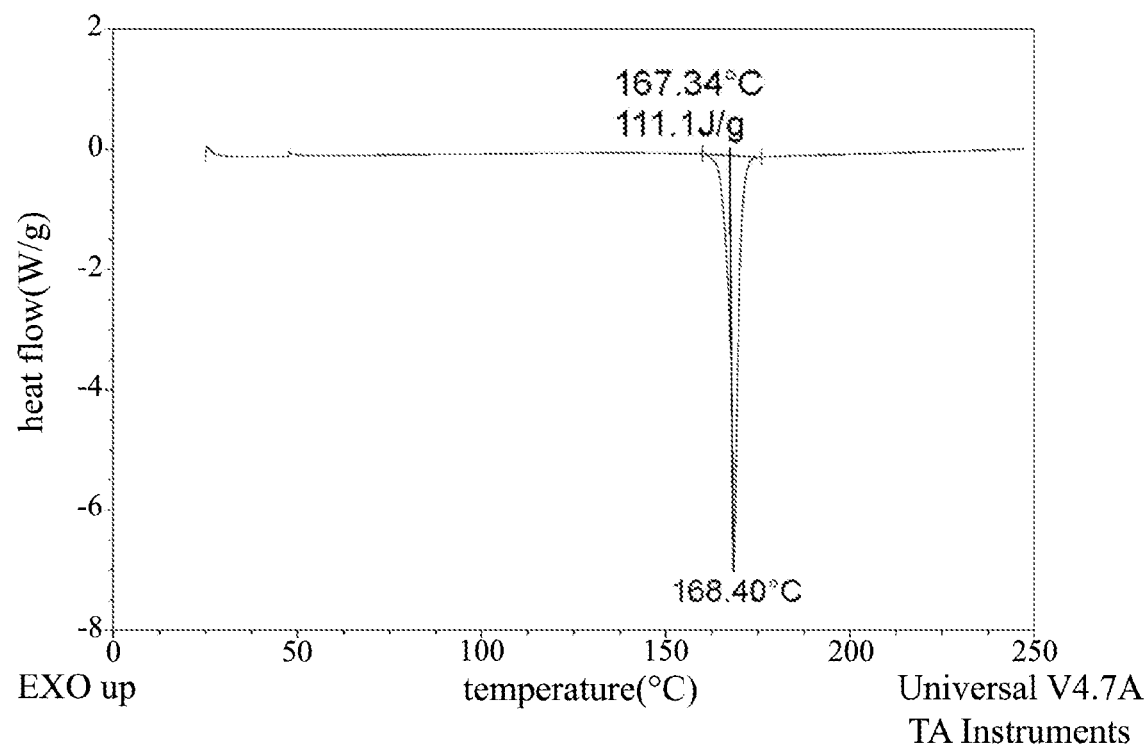
FIG. 2a shows the DSC pattern of the new crystal form of dezocine according to Example 1 of the present application.
Figure 2B:
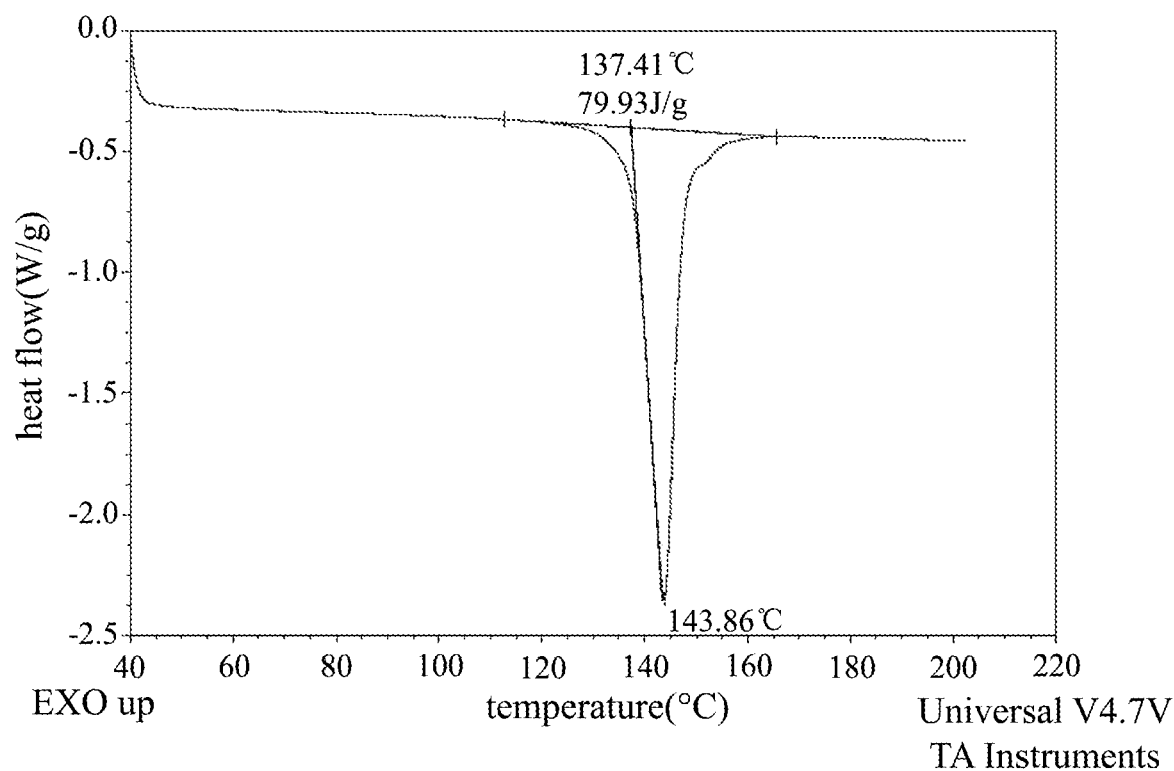
FIG. 2b shows the DSC pattern of the sample obtained from Example 1 of the Patent NO. CN102503840A.

In one embodiment of the present application, there is provided a new crystal form of dezocine, and the characteristics of the DSC pattern of the new crystal form of dezocine can be substantially as shown in FIG. 2a.

Figure 3:
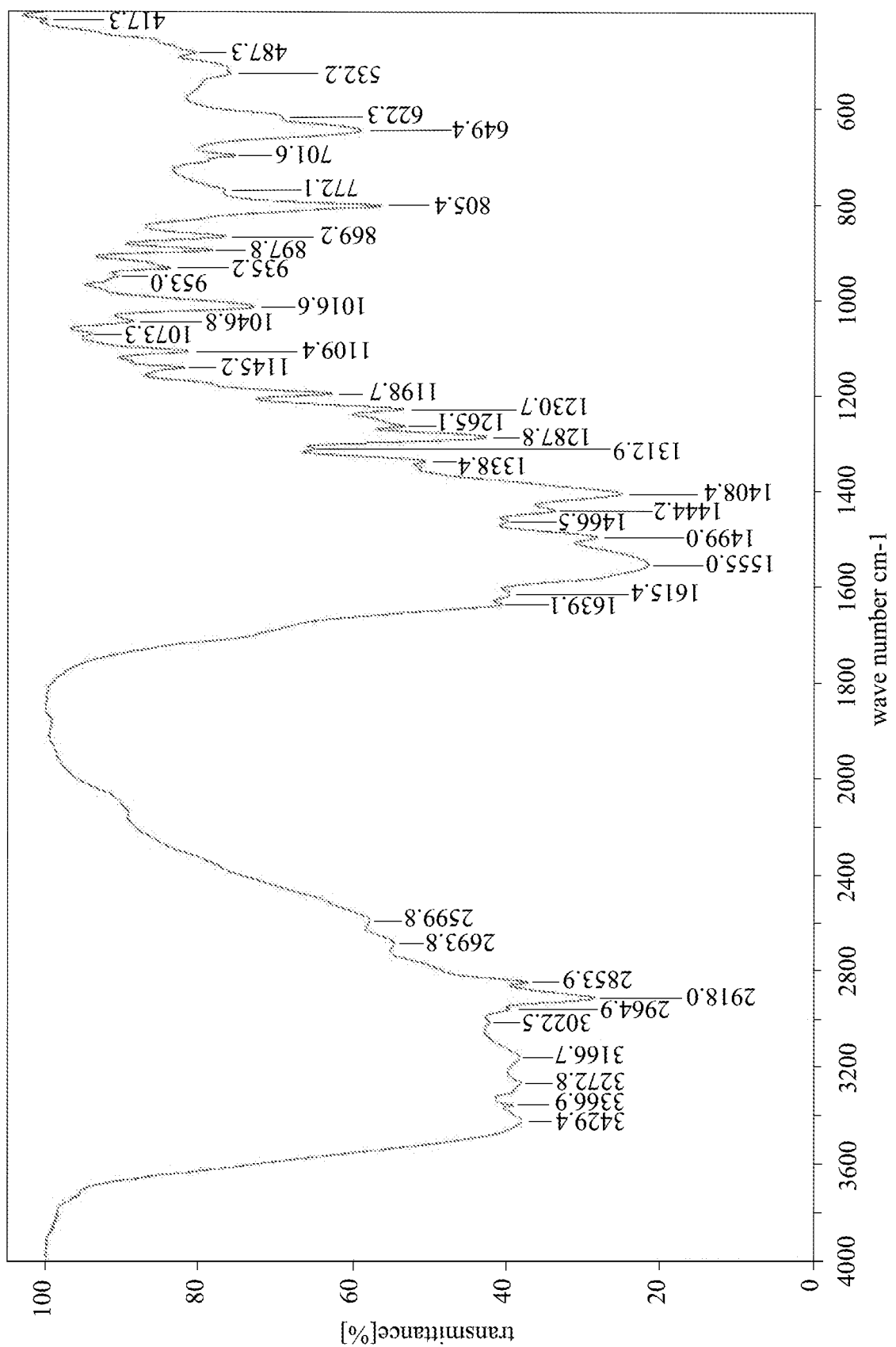
FIG. 3 shows the IR pattern of the new crystal form of dezocine according to Example 1 of the present application.

In one embodiment of the present application, there is provided a new crystal form of dezocine, and the IR data characteristics of the new crystal form of dezocine can be substantially as shown in FIG. 3.

Figure 4:
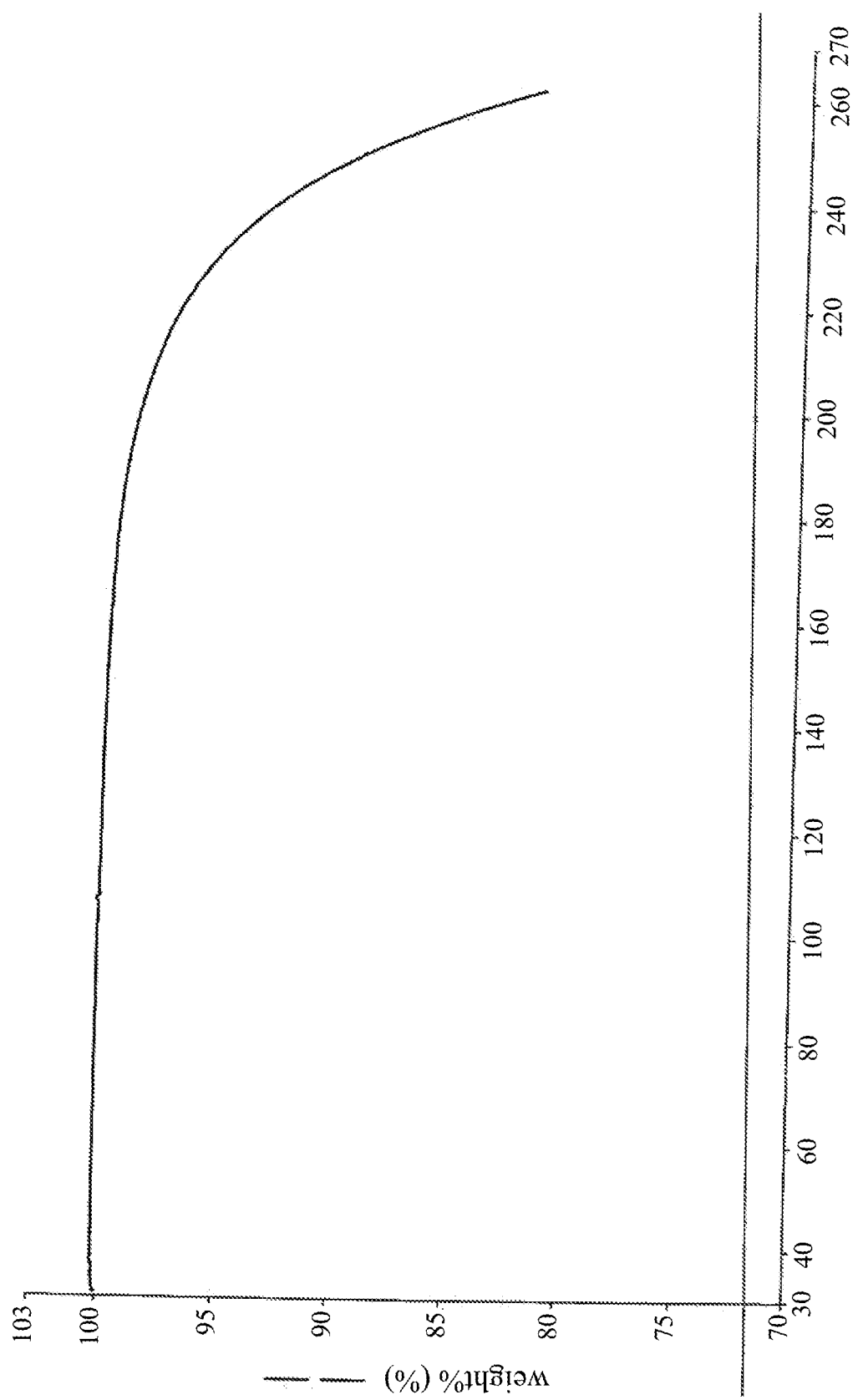
FIG. 4 shows the TGA pattern of the new crystal form of dezocine according to Example 1 of the present application.

In one embodiment of the present application, there is provided a new crystal form of dezocine, and the TGA data characteristics of the new crystal form of dezocine may be substantially as shown in FIG. 4.

In another aspect, in another embodiment of the present application, there is provided a preparation method for the new crystal form of dezocine described above, including the following steps of:

1) under heating, dissolving dezocine in a solvent A in which dezocine has higher solubility, under stirring, then adding another solvent B in which dezocine has lower solubility;

2) precipitating crystals by cooling and heat keeping, after filtering, collecting the crystals, and drying to obtain the crystal form of dezocine.

As used in the present application, the phrase "dissolving dezocine in a solvent A in which dezocine has higher solubility, under stirring, then adding another solvent B in which dezocine has lower solubility" (or "dissolving dezocine in a solvent A in which dezocine is soluble, under stirring, then adding another solvent B in which dezocine is insoluble") means that two solvents with different solubility for dezocine can be selected, the solvent A in which dezocine has high solubility is firstly used for dissolution, and then the other solvent B in which dezocine has low solubility relative to solvent A is added, the claimed new crystal form of dezocine is thereby precipitated.

Specifically, "solvent A in which dezocine has higher solubility" (or "solvent A in which dezocine is soluble") may be a solvent that dissolves more than 0.1 g of dezocine per milliliter of solvent A; and "solvent B in which dezocine has lower solubility" (or "solvent B in which dezocine is insoluble") may be a solvent that dissolves less than 0.03 g of dezocine per milliliter of solvent B.

In an embodiment of the present application, in the preparation method for the new crystal form of dezocine, the solvent A in which dezocine has a higher solubility in step 1) can be selected from one or both of dioxane and ethyl acetate.

In an embodiment of the present application, in the preparation method for the new crystal form of dezocine, the solvent A in which dezocine has a higher solubility in step 1) can be dioxane.

In an embodiment of the present application, in the preparation method for the new crystal form of dezocine, the solvent B in which dezocine has a lower solubility in step 1) can be selected from one or more of acetonitrile, toluene and petroleum ether.

In an embodiment of the present application, in the preparation method for the new crystal form of dezocine, the solvent B in which dezocine has a lower solubility in step 1) can be petroleum ether.

In an embodiment of the present application, in the preparation method for the new crystal form of dezocine, the ratio of the amount of solvent A to the amount of dezocine in step 1) can be dissolving 1 gram of dezocine in 1 ml to 30 ml of solvent A.

In an embodiment of the present application, in the preparation method for the new crystal form of dezocine, the ratio of the amount of solvent A to the amount of dezocine in step 1) can be dissolving 1 gram of dezocine in 2 ml to 10 ml of solvent A.

In an embodiment of the present application, in the preparation method for the new crystal form of dezocine, the volume ratio of solvent A to solvent B in step 1) can be 1:0.3 to 1:10.

In an embodiment of the present application, in the preparation method for the new crystal form of dezocine, the volume ratio of solvent A to solvent B in step 1) can be 1:0.4 to 1:10.

In an embodiment of the present application, in the preparation method for the new crystal form of dezocine, the volume ratio of solvent A to solvent B in step 1) can be 1:0.5 to 1:10.

In an embodiment of the present application, in the preparation method for the new crystal form of dezocine, the volume ratio of solvent A to solvent B in step 1) can be 1:1 to 1:2.5.

In an embodiment of the present application, in the preparation method for the new crystal form of dezocine, the temperature for dissolving under heating in step 1) can be 30° C. to 100° C.

In an embodiment of the present application, in the preparation method for the new crystal form of dezocine, the temperature for dissolving under heating in step 1) can be 70° C. to 80° C.

In an embodiment of the present application, in the preparation method for the new crystal form of dezocine, the temperature for precipitating by cooling in step 2) can be 0° C. to 20° C.

In an embodiment of the present application, in the preparation method for the new crystal form of dezocine, the temperature for precipitating by cooling in step 2) can be 0° C. to 10° C.

In an embodiment of the present application, in the preparation method for the new crystal form of dezocine, the drying in step 2) is drying under vacuum (−0.1 MPa), and the temperature for the drying can be 60° C. to 90° C.

In an embodiment of the present application, in the preparation method for the new crystal form of dezocine, the drying in step 2) is drying under vacuum (−0.1 MPa), and the temperature for the drying can be 60° C. to 80° C.

In an embodiment of the present application, in the preparation method for the new crystal form of dezocine, the dezocine used in step 1) can be prepared by the method according to the Patent No. CN102503840A.

In the third aspect, the present application provides a pharmaceutical composition including the new crystal form of dezocine described above. For the administration mode and dosage of the pharmaceutical composition, the teaching in U.S. Pat. No. 4,001,331 can be referred to.

In the fourth aspect, the present application provides use of the new crystal form of dezocine or a pharmaceutical composition thereof described above in analgesics.

Hereinafter, the technical solution of the present application will be further explained by specific Examples, in order to enable those skilled in the art to better understand the application, but the scope of protection of the present application is not limited thereto.

The dezocine used in Examples is prepared according to the method of Example 1 in Patent No. CN102503840A.

XRD Test Conditions:

Equipment model: BrukerD8advance, Germany; X-ray tube: Cu tube; radiation used: K (α1); voltage and current of generator: 40 kV and 40 mA; step size: 0.02°; scanning speed: 0.5 s/time; scanning range: 3°-40°;

DSC Test Conditions:

Equipment model: TA Q200; equilibrium temperature: 25° C.; temperature rise condition:

the temperature rises to 250° C. at a rate of 10° C./min; nitrogen flow rate: 40 ml/min; aluminum dish, cover;

IR Test Conditions:

Equipment model: Bruker Tensor 27; KBr pellet; scanning range: 4000-400 cm$^{-1}$;

TGA Test Conditions:

Equipment model: NETZSCH TG 209; temperature rise rate: 10° C./min; temperature range: 30-250° C.; crucible material: Al$_2$O$_3$.

Example 1

To a clean 50 ml reaction flask, 2 g of dezocine and 7.5 ml of dioxane were added, after heating to 80° C. with stirring for complete dissolution, 7.5 ml of acetonitrile was added, cooled to about 5° C. and precipitated for 2 h, filtered to obtain a solid, dried at 80° C. under vacuum to give 1.7 g of dry dezocine with a yield of 85%. The XRD pattern of the crystal form of dezocine is determined as shown in FIG. 1a, the DSC pattern is as shown in FIG. 2a, the IR pattern is as shown in FIG. 3, and the TGA pattern is as shown in FIG. 4.

Example 2

To a clean 50 ml reaction flask, 2 g of dezocine and 9 ml of dioxane were added, after heating to 60° C. with stirring for complete dissolution, 6 ml of petroleum ether was added, cooled to about 5° C. and precipitated for 2 h, filtered to obtain a solid, dried at 60° C. under vacuum to give 1.9 g of dry dezocine with a yield of 95%.

Example 3

To a clean 50 ml reaction flask, 2 g of dezocine and 15 ml of ethyl acetate were added, after heating to 60° C. with stirring for complete dissolution, 6 ml of petroleum ether was added, cooled to about 15° C. and precipitated for 2 h, filtered to obtain a solid, dried at 80° C. under vacuum to give 1.3 g of dry dezocine with a yield of 65%.

Example 4

To a clean 50 ml reaction flask, 2 g of dezocine and 15 ml of ethyl acetate were added, after heating to 65° C. with stirring for complete dissolution, 10 ml of toluene was added, cooled to about 10° C. and precipitated for 2 h, filtered to obtain a solid, dried at 70° C. under vacuum to give 1.6 g of dry dezocine with a yield of 80%.

Example 5

To a clean 50 ml reaction flask, 2 g of dezocine and 9 ml of dioxane were added, after heating to 75° C. with stirring for complete dissolution, 15 ml of toluene was added, cooled to about 5° C. and precipitated for 2 h, filtered to obtain a solid, dried at 90° C. under vacuum to give 1.4 g of dry dezocine with a yield of 70%.

The typical XRD pattern of the crystal form of dezocine obtained in Examples of the present application is as shown in FIG. 1a, the DSC pattern is as shown in FIG. 2a, the IR pattern is as shown in FIG. 3, and the TGA pattern is as shown in FIG. 4.

Figure 1B:
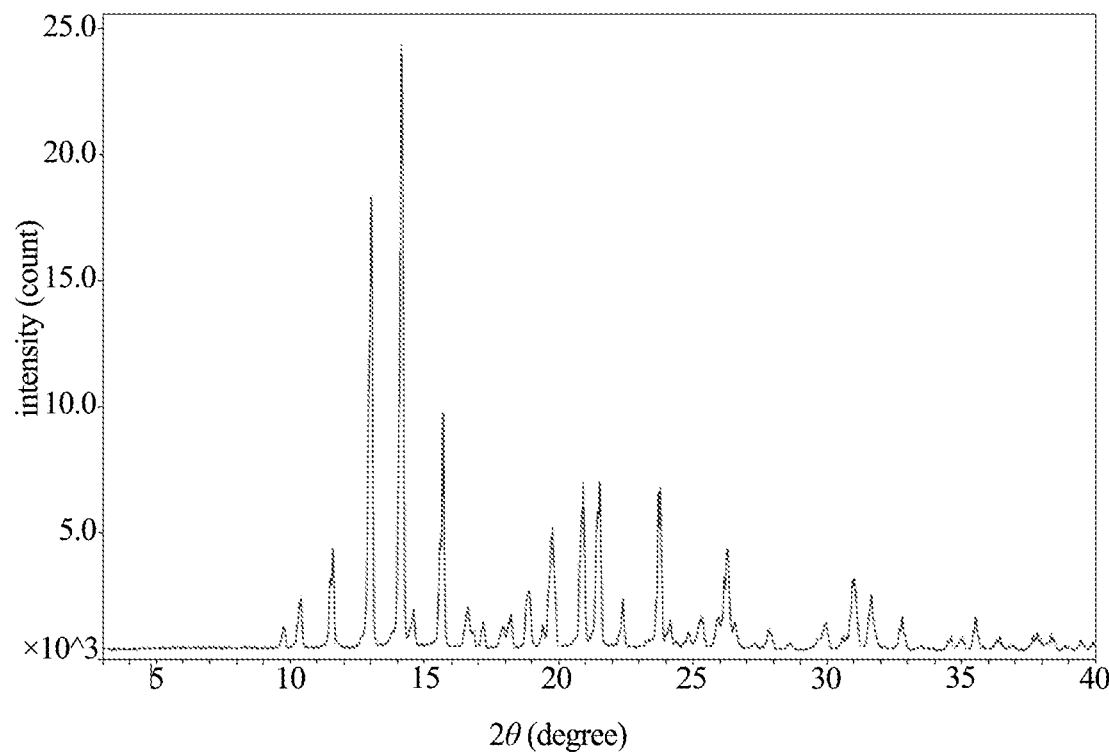
FIG. 1b shows the XRD pattern of the sample obtained from Example 1 of the Patent No. CN102503840A.

The dezocine crystal obtained in the Patent No. CN102503840A (hereinafter referred to as crystal form I of dezocine) is tested in the present application, its X-ray powder diffraction pattern is determined using Cu/K-α1, as shown in FIG. 1b, and has the following diffraction peak profile:

| Peak number | 2θ | d value | Height % | Area % | FWHM |
|---|---|---|---|---|---|
| 1 | 9.750 | 9.0639 | 3.5 | 3.6 | 0.148 |
| 2 | 10.398 | 8.5007 | 8.4 | 8.4 | 0.147 |
| 3 | 11.585 | 7.6319 | 16.4 | 17.0 | 0.152 |
| 4 | 13.008 | 6.8000 | 75.1 | 74.6 | 0.145 |
| 5 | 14.150 | 6.2537 | 100.0 | 100.0 | 0.146 |
| 6 | 14.604 | 6.0606 | 5.9 | 6.6 | 0.164 |
| 7 | 15.688 | 5.6439 | 38.6 | 28.7 | 0.109 |
| 8 | 16.615 | 5.3313 | 6.6 | 9.7 | 0.215 |
| 9 | 17.188 | 5.1548 | 4.5 | 3.8 | 0.122 |
| 10 | 17.938 | 4.9408 | 3.8 | 5.4 | 0.212 |
| 11 | 18.200 | 4.8704 | 5.5 | 6.3 | 0.166 |
| 12 | 18.888 | 4.6945 | 9.4 | 11.8 | 0.185 |
| 13 | 19.403 | 4.5710 | 3.7 | 4.3 | 0.173 |
| 14 | 19.773 | 4.4863 | 19.7 | 26.4 | 0.196 |
| 15 | 20.918 | 4.2433 | 27.1 | 31.8 | 0.172 |
| 16 | 21.531 | 4.1238 | 27.1 | 32.5 | 0.175 |
| 17 | 22.399 | 3.9659 | 7.9 | 6.6 | 0.122 |
| 18 | 23.798 | 3.7358 | 26.4 | 48.9 | 0.271 |
| 19 | 24.173 | 3.6787 | 4.3 | 5.9 | 0.202 |
| 20 | 24.828 | 3.5831 | 2.6 | 2.6 | 0.150 |
| 21 | 25.302 | 3.5171 | 4.9 | 7.5 | 0.222 |
| 22 | 25.950 | 3.4307 | 4.9 | 13.8 | 0.410 |
| 23 | 26.286 | 3.3876 | 16.2 | 25.6 | 0.231 |
| 24 | 26.564 | 3.3528 | 4.3 | 8.1 | 0.273 |
| 25 | 27.827 | 3.2034 | 3.2 | 3.9 | 0.179 |
| 26 | 29.958 | 2.9802 | 4.3 | 7.9 | 0.272 |
| 27 | 31.024 | 2.8802 | 11.4 | 19.0 | 0.244 |
| 28 | 31.657 | 2.8240 | 8.6 | 10.9 | 0.187 |
| 29 | 32.818 | 2.7267 | 5.4 | 6.2 | 0.168 |
| 30 | 33.548 | 2.6691 | 0.7 | 1.5 | 0.304 |
| 31 | 34.615 | 2.5892 | 2.2 | 2.7 | 0.180 |
| 32 | 35.029 | 2.5595 | 2.1 | 3.5 | 0.240 |
| 33 | 35.526 | 2.5248 | 5.3 | 5.2 | 0.143 |
| 34 | 36.431 | 2.4642 | 2.1 | 2.9 | 0.208 |
| 35 | 36.851 | 2.4371 | 0.8 | 1.1 | 0.203 |
| 36 | 37.850 | 2.3750 | 2.9 | 7.1 | 0.359 |
| 37 | 38.362 | 2.3444 | 2.2 | 5.3 | 0.348 |
| 38 | 39.471 | 2.2811 | 1.7 | 1.8 | 0.154 |

After solubility and stability tests, the inventors surprisingly found that the solubility and stability of the new crystal form of dezocine of the present application (hereinafter referred to as crystal Form II of dezocine) are significantly better than those of crystal Form I of dezocine.

i. Compared with the sample of crystal Form I of dezocine, the new crystal form of dezocine according to the present application has better solubility in 0.1 mol/L hydrochloric acid solution, and the solubility is increased by about 32%, as shown in the following table:

| Sample | Amount of sample | Amount of solvent | Solubility |
|---|---|---|---|
| Crystal Form II of dezocine | 50 mg | 1.5 ml | 0.033 g/ml |
| Crystal Form I of dezocine | 50 mg | 2.0 ml | 0.025 g/ml | ii. Compared with the sample of crystal Form I of dezocine, the content of related substances in the new crystal Form of dezocine according to the present application is lower, as shown in the following table for details:

| Sample | Crystal Form I | Example 1 | Example 2 | Example 3 | Example 4 | Example 5 |
|---|---|---|---|---|---|---|
| Related substances | 0.08% | 0.06% | 0.07% | 0.04% | 0.06% | 0.04% | iii. Compared with the sample of crystal Form I of dezocine, the new crystal form of dezocine prepared according to the present application has better stability, and changes of the related substances within the new crystal form of dezocine over 6 months are as follows:

| Sample | 0 days | 1 month | 3 months | 6 months |
|---|---|---|---|---|
| Crystal Form I of dezocine | 0.08% | 0.15% | 0.21% | 0.28% |
| Example 1 | 0.06% | 0.07% | 0.10% | 0.13% |
| Example 2 | 0.07% | 0.09% | 0.10% | 0.12% |
| Example 3 | 0.04% | 0.05% | 0.8% | 0.10% |
| Example 4 | 0.06% | 0.08% | 0.10% | 0.12% |
| Example 5 | 0.04% | 0.06% | 0.07% | 0.09% | iv. Compared with the sample of crystal Form I of dezocine, the new crystal form of dezocine prepared according to the present application has better stability, and changes of the content of impurity B over 6 months are as follows:

| Sample | 0 days | 1 month | 3 months | 6 months |
|---|---|---|---|---|
| Crystal Form I of dezocine | 0.03% | 0.04% | 0.04% | 0.05% |
| Example 1 | Not detected | Not detected | Not detected | Not detected |
| Example 2 | Not detected | Not detected | Not detected | Not detected |
| Example 3 | Not detected | Not detected | Not detected | Not detected |
| Example 4 | Not detected | Not detected | Not detected | Not detected |
| Example 5 | Not detected | Not detected | Not detected | Not detected | v. Crystal Form I of dezocine has been refined for many times according to Patent No. CN102503840A, while the content of impurity B is constant, as shown in the following table:

|  | Crystal Form I of dezocine | Primary refining | Secondary refining | Triple refining |
|---|---|---|---|---|
| Content of impurity B | 0.03% | 0.03% | 0.03% | 0.03% |

Therefore, the new crystal form of dezocine provided by the present application has better solubility and is beneficial to medication dissolution and absorption by human body; it has better stability and lower content of related substances during storage; meanwhile, the preparation method for the new crystal form has the advantages such as simple operations, good reproducibility, suitability for industrial mass production and the like.

What is claimed is:

1. A crystal form of dezocine, wherein the X-ray powder diffraction (XRD) pattern of the crystal form of dezocine is determined using Cu/K-al and has diffraction peaks at 2θ value of 9.1±0.2, 12.2±0.2, 13.0±0.2, 13.6±0.2, 14.0±0.2, 14.7±0.2, 15.2±0.2, 19.6±0.2, 23.1±0.2, 24.4.4±0.2, and 27.2±0.2, with the height % of the diffraction peaks greater than 20.

2. The crystal form of dezocine according to claim 1, wherein the X-ray powder diffraction pattern of the crystal form of dezocine is determined using Cu/K-α1, and has the following diffraction peak profile:

| Peak number | 2θ | d value | Height % | Area % | FWHM |
|---|---|---|---|---|---|
| 1 | 9.100 | 9.7102 | 51.4 | 66.1 | 0.460 |
| 2 | 12.161 | 7.2716 | 100.00 | 100.0 | 0.358 |
| 3 | 13.008 | 6.8003 | 23.0 | 9.2 | 0.143 |
| 4 | 13.556 | 6.5265 | 41.8 | 22.3 | 0.191 |
| 5 | 13.973 | 6.3329 | 52.2 | 26.2 | 0.179 |
| 6 | 14.743 | 6.0038 | 98.7 | 72.5 | 0.263 |
| 7 | 15.197 | 5.8252 | 56.3 | 44.9 | 0.285 |
| 8 | 16.656 | 5.3183 | 4.2 | 2.5 | 0.208 |
| 9 | 17.051 | 5.1958 | 7.7 | 3.9 | 0.183 |
| 10 | 18.118 | 4.8923 | 12.1 | 9.2 | 0.271 |
| 11 | 18.452 | 4.8043 | 14.7 | 17.4 | 0.424 |
| 12 | 19.186 | 4.6222 | 13.0 | 9.7 | 0.266 |
| 13 | 19.598 | 4.5259 | 19.8 | 12.8 | 0.231 |
| 14 | 21.808 | 4.0720 | 14.8 | 8.4 | 0.202 |
| 15 | 22.675 | 3.9182 | 8.1 | 6.2 | 0.273 |
| 16 | 23.111 | 3.8452 | 74.9 | 42.2 | 0.201 |
| 17 | 23.444 | 3.7914 | 8.9 | 7.9 | 0.318 |
| 18 | 24.355 | 3.6516 | 25.5 | 22.9 | 0.321 |
| 19 | 24.865 | 3.5779 | 6.9 | 5.9 | 0.307 |
| 20 | 25.580 | 3.4794 | 6.0 | 4.7 | 0.276 |
| 21 | 27.159 | 3.2807 | 19.9 | 12.4 | 0.223 |
| 22 | 27.549 | 3.2351 | 3.0 | 3.6 | 0.425 |
| 23 | 28.043 | 3.1792 | 4.5 | 4.2 | 0.337 |
| 24 | 28.281 | 3.1530 | 5.6 | 3.7 | 0.236 |
| 25 | 29.859 | 2.9899 | 1.8 | 1.1 | 0.215 |
| 26 | 30.274 | 2.9498 | 5.9 | 5.1 | 0.311 |
| 27 | 30.773 | 2.9031 | 2.6 | 2.1 | 0.281 |
| 28 | 31.635 | 2.8259 | 1.2 | 0.6 | 0.178 |
| 29 | 32.467 | 2.7554 | 2.7 | 2.1 | 0.275 |
| 30 | 33.201 | 2.6962 | 1.6 | 0.5 | 0.108 |
| 31 | 33.865 | 2.6448 | 3.7 | 2.2 | 0.215 |
| 32 | 34.519 | 2.5962 | 1.1 | 0.8 | 0.271 |
| 33 | 36.000 | 2.4927 | 5.6 | 4.5 | 0.286 |
| 34 | 37.715 | 2.3832 | 5.4 | 4.6 | 0.310 |
| 35 | 39.298 | 2.2908 | 3.3 | 1.5 | 0.158. |

3. The crystal form of dezocine according to claim 1, wherein a DSC test of the crystal form of dezocine shows an endothermic peak near 168.40° C.

4. The crystal form of dezocine according to claim 1, wherein IR data characteristics of the crystal form of dezocine is substantially as shown in FIG. 3.

5. The crystal form of dezocine according to claim 1, wherein TGA data characteristics of the crystal form of dezocine is substantially as shown in FIG. 4.

6. A preparation method for the crystal form of dezocine according to claim 1, comprising the following steps of:
  1) under heating, dissolving dezocine in a solvent A in which dezocine is soluble, under stirring, then adding another solvent B in which dezocine is insoluble;
  2) precipitating crystals by cooling and heat keeping, after filtering, collecting the crystals, and drying to obtain the crystal form of dezocine.

7. The preparation method according to claim 6, wherein the solvent A is selected from one or both of dioxane and ethyl acetate, and is optionally dioxane.

8. The preparation method according to claim 6, wherein the solvent B is selected from one or more of acetonitrile, toluene, petroleum ether, and ethyl ether, and is optionally petroleum ether.

9. The preparation method according to claim 6, wherein, the ratio of the amount of the solvent A to the amount of dezocine in step 1) is dissolving 1 gram of dezocine in 1 ml to 30 ml, optionally in 2 ml to 10 ml, of the solvent A; wherein the volume ratio of the solvent A to the solvent B is 1:0.3 to 1:10, optionally 1:1 to 1:2.5.

10. The preparation method according to claim 6, wherein the temperature for dissolving under heating in step 1) is 30° C. to 100° C., optionally 70° C. to 80° C.

11. The preparation method according to claim 6, wherein the temperature for precipitating by cooling in step 2) is 0° C. to 20° C., optionally 0° C. to 10° C.

12. The preparation method according to claim 6, wherein the drying in step 2) is drying under vacuum, and the temperature for the drying is 60° C. to 90° C., optionally 60° C. to 80° C.

13. A preparation method for the crystal form of dezocine according to claim 2, comprising the following steps of:
1) under heating, dissolving dezocine in a solvent A in which dezocine is soluble, under stirring, then adding another solvent B in which dezocine is insoluble;
2) precipitating crystals by cooling and heat preservation, after filtering, collecting the crystals, and drying to obtain the crystal form of dezocine.

14. A preparation method for the crystal form of dezocine according to claim 3, comprising the following steps of:
1) under heating, dissolving dezocine in a solvent A in which dezocine is soluble, under stirring, then adding another solvent B in which dezocine is insoluble;
2) precipitating crystals by cooling and heat preservation, after filtering, collecting the crystals, and drying to obtain the crystal form of dezocine.

15. A preparation method for the crystal form of dezocine according to claim 4, comprising the following steps of:
1) under heating, dissolving dezocine in a solvent A in which dezocine is soluble, under stirring, then adding another solvent B in which dezocine is insoluble;
2) precipitating crystals by cooling and heat preservation, after filtering, collecting the crystals, and drying to obtain the crystal form of dezocine.

16. A preparation method for the crystal form of dezocine according to claim 5, comprising the following steps of:
1) under heating, dissolving dezocine in a solvent A in which dezocine is soluble, under stirring, then adding another solvent B in which dezocine is insoluble;
2) precipitating crystals by cooling and heat preservation, after filtering, collecting the crystals, and drying to obtain the crystal form of dezocine.

* * * * *